US009810844B2

(12) United States Patent
Reever

(10) Patent No.: US 9,810,844 B2
(45) Date of Patent: Nov. 7, 2017

(54) METHODS AND APPARATUS RELATED TO A SIDE-FIRE OPTICAL FIBER HAVING A ROBUST DISTAL END PORTION

(71) Applicant: Boston Scientific Scimed, Inc., Maple Grove, MN (US)

(72) Inventor: Kenneth Reever, Hopedale, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 88 days.

(21) Appl. No.: 14/275,499

(22) Filed: May 12, 2014

(65) Prior Publication Data

US 2015/0253505 A1 Sep. 10, 2015

Related U.S. Application Data

(63) Continuation of application No. 13/025,285, filed on Feb. 11, 2011, now Pat. No. 8,724,941.
(Continued)

(51) Int. Cl.
*G02B 6/42* (2006.01)
*G02B 6/26* (2006.01)
(Continued)

(52) U.S. Cl.
CPC .............. *G02B 6/262* (2013.01); *A61B 18/24* (2013.01); *G02B 1/14* (2015.01); *G02B 6/443* (2013.01);
(Continued)

(58) Field of Classification Search
CPC ............ G02B 6/2551; A61B 1/001777; A61B 1/0615
See application file for complete search history.

(56) References Cited

U.S. PATENT DOCUMENTS 4,718,417 A 1/1988 Kittrell et al.
4,740,047 A 4/1988 Abe et al.
(Continued)

FOREIGN PATENT DOCUMENTS

EP 0 195 375 A2 9/1986

OTHER PUBLICATIONS

U.S. Appl. No. 12/947,365, filed Nov. 16, 2010, with transmittal letter, specification, drawings, and abstract (64 pages).
(Continued)

*Primary Examiner* — Sung Pak
*Assistant Examiner* — Hoang Tran
(74) *Attorney, Agent, or Firm* — Bookoff McAndrews, PLLC

(57) ABSTRACT

An aspect of the present disclosure may include an apparatus having an optical waveguide. The optical waveguide may have a distal end surface non-normal to a longitudinal centerline of a distal end portion of the optical waveguide, wherein the distal end surface may define a portion of an interface configured to redirect electromagnetic radiation propagated from within the optical waveguide and incident on the portion of the interface to a direction offset from the longitudinal centerline. The apparatus may further include a capillary component which may have a first portion of an inner surface heat-fused to a portion of an outer surface of the optical waveguide. The apparatus may also include a reinforcement component which may have a proximal end surface disposed distal to the distal end surface of the optical waveguide such that the distal end surface of the optical waveguide and the proximal end surface of the reinforcement component may be separated by a non-zero distance, and wherein a portion of an outer surface of the reinforcement component may be heat-fused to a second portion of the inner surface of the capillary component.

13 Claims, 7 Drawing Sheets

Related U.S. Application Data

(60) Provisional application No. 61/306,755, filed on Feb. 22, 2010.

(51) Int. Cl.
 *A61B 18/24* (2006.01)
 *G02B 1/14* (2015.01)
 *G02B 6/44* (2006.01)
 *A61B 18/22* (2006.01)

(52) U.S. Cl.
 CPC .... *G02B 6/4494* (2013.01); *A61B 2018/2272* (2013.01)

(56) References Cited

U.S. PATENT DOCUMENTS

| | | | |
|---|---|---|---|
| 5,242,438 A | 9/1993 | Saadatmanesh et al. | |
| 5,254,114 A | 10/1993 | Reed, Jr. et al. | |
| 5,257,991 A * | 11/1993 | Fletcher | A61B 5/0084 606/15 |
| 5,343,543 A | 8/1994 | Novak, Jr. et al. | |
| 5,354,294 A | 10/1994 | Chou | |
| 5,437,660 A | 8/1995 | Johnson et al. | |
| 5,509,917 A | 4/1996 | Cecchetti et al. | |
| 5,537,499 A | 7/1996 | Brekke | |
| 5,562,657 A * | 10/1996 | Griffin | A61B 18/245 606/13 |
| 5,638,483 A | 6/1997 | Konwitz | |
| 5,649,924 A | 7/1997 | Everett et al. | |
| 5,772,657 A | 6/1998 | Hmelar et al. | |
| 5,833,683 A | 11/1998 | Fuller et al. | |
| 5,993,380 A | 11/1999 | Yabe et al. | |
| 6,296,608 B1 | 10/2001 | Daniels et al. | |
| 6,445,939 B1 | 9/2002 | Swanson et al. | |
| 6,576,163 B2 | 6/2003 | Mersch | |
| 6,615,072 B1 | 9/2003 | Izatt et al. | |
| 6,620,154 B1 | 9/2003 | Amirkhanian et al. | |
| 6,891,984 B2 | 5/2005 | Petersen et al. | |
| 7,108,692 B2 | 9/2006 | Frenz et al. | |
| 7,169,140 B1 | 1/2007 | Kume | |
| 7,447,409 B2 | 11/2008 | Griffin | |
| 7,463,801 B2 | 12/2008 | Brekke et al. | |
| 7,492,987 B2 | 2/2009 | Yeik et al. | |
| 2007/0106286 A1 | 5/2007 | Harschack et al. | |
| 2008/0247714 A1 | 10/2008 | Nakamura et al. | |
| 2009/0287199 A1 | 11/2009 | Hanley et al. | |
| 2010/0016845 A1 * | 1/2010 | Hanley | A61B 18/24 606/15 |
| 2010/0198009 A1 | 8/2010 | Farr et al. | |
| 2011/0038580 A1 * | 2/2011 | Griffin | A61B 18/24 385/33 |

OTHER PUBLICATIONS

Written Opinion and International Search Authority for corresponding International Application No. PCT/US2011/024440, dated Feb. 23, 2012, 10 pages.

International Search Report for corresponding International Application No. PCT/US2011/024440, dated Feb. 23, 2012, 12 pages.

Invitation to Pay Additional Fees and Partial International Search Report for corresponding International Application No. PCT/US2011/024440, dated Dec. 15, 2011, 6 pages.

* cited by examiner

METHODS AND APPARATUS RELATED TO A SIDE-FIRE OPTICAL FIBER HAVING A ROBUST DISTAL END PORTION

CROSS REFERENCE TO RELATED APPLICATION

This Nonprovisional Patent Application is a continuation of U.S. patent application Ser. No. 13/025,285, filed Feb. 11, 2011, which claims the benefit of priority under 35 U.S.C. § 119 to U.S. Provisional Patent Application No. 61/306,755, filed Feb. 22, 2010, and titled "METHODS AND APPARATUS RELATED TO A SIDE-FIRE OPTICAL FIBER HAVING A ROBUST DISTAL END PORTION," the entirety of each being incorporated herein by reference.

FIELD OF THE INVENTION

Embodiments relate generally to optical medical devices, and, in particular, to side-fire optical fiber members and methods for using such devices.

BACKGROUND OF THE INVENTION

During some laser-based surgical procedures, a side-fire optical fiber member (also can be referred to as a side-fire member) can provide a medical practitioner with more control than a straight-firing optical fiber system when applying laser energy to a treatment area involving an off-axis location. For example, laser energy can be emitted towards a target area in a lateral direction via an angled surface of an optical waveguide of the side-fire optical fiber member. Even if carefully manufactured using known manufacturing techniques, a side-fire optical fiber member can be susceptible to, for example, undesirable laser energy leakage and/or premature structural failure. For example, light intensity from laser energy emitted from a distal end portion of the side-fire optical fiber member can boil a fluid around the distal end portion of the side-fire optical fiber member causing a cavitation bubble. A shockwave (e.g., an acoustic shockwave) produced when the cavitation bubble collapses around the distal end portion of the side-fire optical fiber member can damage the distal end portion of the side-fire optical fiber member.

Thus, a need exists for methods and apparatus related to a side-fire optical fiber member that can increase device longevity, increase laser energy transmission efficiency, reduce overheating, and/or increase patient safety.

SUMMARY OF THE INVENTION

An aspect of the present disclosure may include an apparatus having an optical waveguide. The optical waveguide may have a distal end surface non-normal to a longitudinal centerline of a distal end portion of the optical waveguide, wherein the distal end surface may define a portion of an interface configured to redirect electromagnetic radiation propagated from within the optical waveguide and incident on the portion of the interface to a direction offset from the longitudinal centerline. The apparatus may further include a capillary component which may have a first portion of an inner surface heat-fused to a portion of an outer surface of the optical waveguide. The apparatus may also include a reinforcement component which may have a proximal end surface disposed distal to the distal end surface of the optical waveguide such that the distal end surface of the optical waveguide and the proximal end surface of the reinforcement component may be separated by a non-zero distance, and wherein a portion of an outer surface of the reinforcement component may be heat-fused to a second portion of the inner surface of the capillary component.

Various embodiments of the disclosure may include one or more of the following aspects; the reinforcement component may include an outer diameter substantially the same as an outer diameter of the optical waveguide; a third portion of the inner surface of the capillary component and a distal end surface of the reinforcement component may define an enclosure; the distal end surface of the optical waveguide may be substantially parallel to the proximal end surface of the reinforcement component; the proximal end surface of the reinforcement component may be made of a reflective material; a center portion of the proximal end surface of the reinforcement component may be separated from a center portion of the distal end surface of the optical waveguide by less than a hundredth of an inch; the reinforcement component may be made of a silica-based material that substantially corresponds with a silica-based material of at least one of a core of the optical waveguide and a cladding of the optical waveguide; the reinforcement component may include a hardness substantially corresponding to a hardness of a core portion of the optical waveguide; the reinforcement component may include a coefficient of thermal expansion substantially corresponding to a coefficient of thermal expansion of at least one of a core of the optical waveguide and a cladding of the optical waveguide; the apparatus may further include a gap between the distal end surface of the optical waveguide and the proximal end surface of the reinforcement component, wherein the gap may be fluidically isolated from an enclosure defined by a third portion of the inner surface of the capillary component and a distal end surface of the reinforcement component; an entire circumference of a cross-sectional portion of the outer surface of the optical waveguide may be heat-fused to the first portion of the inner surface of the capillary component; and an entire circumference of a cross-sectional portion of the reinforcement component may be heat-fused to the first portion of the inner surface of the capillary component.

An aspect of the present disclosure may include a method comprising receiving an optical waveguide having a distal end surface non-normal to a longitudinal centerline of a distal end portion of the optical waveguide, wherein the distal end surface may define a portion of an interface configured to redirect electromagnetic radiation propagated from within the optical waveguide and incident on the portion of the interface to a direction offset from the longitudinal centerline. The method may further include disposing a reinforcement component distal to and separate from the distal end surface of the optical waveguide, and moving an inner surface of a capillary component over the distal end surface of the optical waveguide. Additionally, the method may further include heating the capillary component and the optical waveguide such that a portion of the inner surface of the capillary component may be fused to a portion of an outer surface of the optical waveguide and fused to a portion of the reinforcement component.

Various embodiments of the disclosure may include one or more of the following aspects: the method may further include moving the inner surface of the capillary component over an outer surface of the reinforcement component; the method may further include moving the reinforcement component into a bore defined by the inner surface of the capillary component; the method may further include heating a distal end of the capillary component such that an enclosure may be defined by the distal end of the reinforcement component and the capillary component; and a distal end portion of the capillary component may define a cap, and a proximal end portion of the capillary component may define an opening, and wherein the moving of the inner surface of the capillary component may include moving the opening over the distal end surface of the optical waveguide.

An aspect of the present disclosure may include an apparatus comprising a capillary component and a coating disposed substantially around an outer surface of the capillary component, wherein the coating may have a hardness greater than the outer surface of the capillary component. The apparatus may further include an optical waveguide. The optical waveguide may have a portion of an outer surface heat-fused to a portion of an inner surface of the capillary component. The optical waveguide may include a distal end surface non-normal to a longitudinal centerline of a distal end portion of the optical waveguide, and the distal end surface of the optical waveguide may be configured to reflect electromagnetic radiation propagated along a longitudinal axis of a distal end portion of the optical waveguide in a lateral direction through the inner surface of the capillary component and at least a portion of the coating. Further, the coating may be substantially transparent to a spectral region of the electromagnetic radiation.

Various embodiments of the disclosure may include one or more of the following aspects: the coating may be a multilayer coating; and the coating may be one of a diamond-like coating and a magnesium-based coating.

An aspect of the present disclosure may include an apparatus comprising a distal end surface of a side-fire laser fiber which may be defined by a silica-based capillary component and a distal end portion of an optical waveguide. The silica-based capillary component may be heat-fused to at least a portion of an outer surface of the optical waveguide. The distal end surface may be substantially within a plane non-normal to a longitudinal centerline of the optical waveguide such that the plane and the longitudinal centerline may define an angle of less than 20 degrees.

An aspect of the present disclosure may include an apparatus comprising a capillary component and an optical waveguide that may have a first portion of an outer surface heat-fused to a first portion of an inner surface of the capillary component. The optical waveguide may have a distal end surface non-normal to a longitudinal centerline of a distal end portion of the optical waveguide. The distal end surface of the optical waveguide may be configured to reflect electromagnetic radiation propagated along a longitudinal axis of a distal end portion of the optical waveguide in a lateral direction through the first portion of the outer surface of the optical waveguide. The optical waveguide may have a second portion of the outer surface in contact with a second portion of an inner surface of the capillary component without being heat-fused to the second portion of the inner surface of the capillary component. The second portion of the outer surface of the optical waveguide may be on an opposite side of the optical waveguide from the first portion of the outer surface of the optical waveguide.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

The accompanying drawings, which are incorporated in and constitute a part of this specification, illustrate several embodiments of the invention and together with the description, serve to explain the principles of the invention.

DESCRIPTION OF THE EMBODIMENTS

Figure 1:
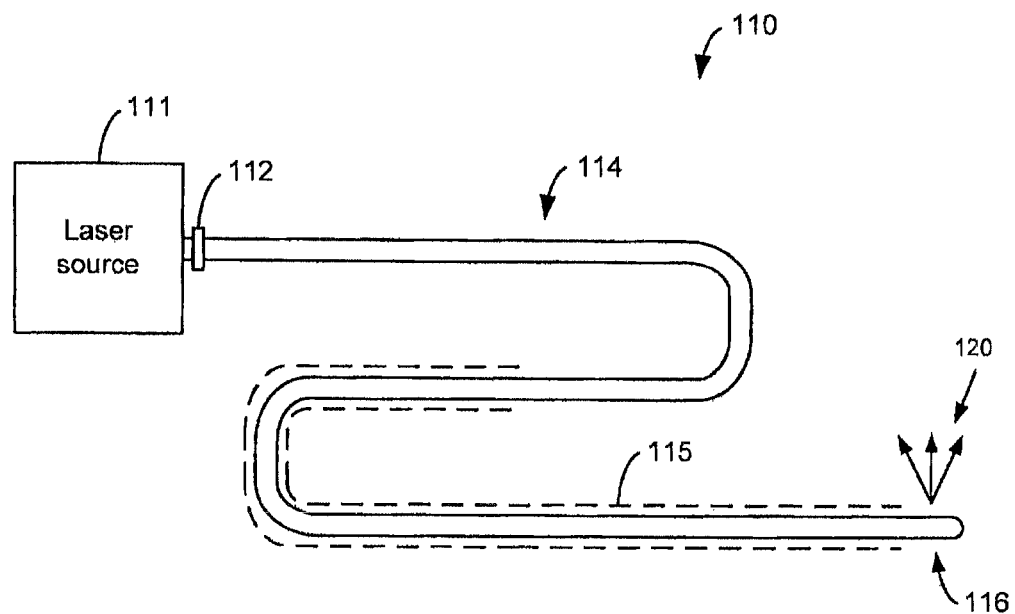
FIG. 1 is a schematic diagram of a side-fire system, according to an embodiment.

Reference will now be made in detail to the present embodiments of the invention, examples of which are illustrated in the accompanying drawings. Wherever possible, the same reference numbers will be used throughout the drawings to refer to the same or like parts.

The devices and methods described herein are generally related to a side-fire member configured to treat an area within a body of a patient. Specifically, the side-fire member can be used to transmit electromagnetic radiation (e.g., electromagnetic radiation in the form of laser energy from a laser source) to a target treatment area that is disposed lateral to a distal end portion (e.g., a side-fire assembly) of the side-fire member. The electromagnetic radiation can be transmitted into and/or propagated within an optical waveguide of the side-fire member. The proximal end portion of the side-tire member can be coupled to the laser source while the distal end portion of the side-fire member can be inserted into the patient's body to provide the laser treatment.

In some embodiments, the optical waveguide of the side-fire member can include, for example, a fiber core, one or more cladding layers disposed around the fiber core, and/or a buffer layer disposed around the cladding layer(s). In some embodiments, the side-fire member can also have a jacket (e.g., a jacket layer disposed around the buffer layer). The jacket can also be referred to as a jacket coating, and the buffer layer can be referred to as a buffer coating. In some embodiments, the buffer layer can function as a cladding layer (can be referred to as a cladding layer).

The optical waveguide of the side-fire member can have a surface non-normal and non-parallel to a longitudinal axis (or centerline) of a distal end portion of the optical fiber. The surface can be referred to as an angled surface and can be at the distal end of the optical waveguide. The angled surface can define at least a portion of an interface (can be referred to as a reflective interface) configured to redirect laser energy propagated from within the optical waveguide and incident on the interface to a direction offset (e.g., a lateral direction, a side-firing direction) from the longitudinal axis toward the target treatment area. The laser energy redirected via the interface can be referred to as lateral laser energy, redirected laser energy, or side-fired laser energy. Because the optical waveguide is configured to redirect laser energy in, for example, a lateral direction, the optical waveguide can be referred to as a side-fire optical waveguide. The optical waveguide and/or laser source can be included in a side-fire system (also can be referred to as an side-fire optical fiber system).

In some embodiments, the side-fire member can have a distal end portion configured so that it is relatively resistant to, for example, damage (e.g., damage caused by a collapsing cavitation bubble) when used during a medical procedure and/or during manufacture of the side-fire member. For example, in some embodiments, the side-fire member can have a reinforcement component disposed inside of a capillary component of the side-fire member. The reinforcement component can be configured so that the capillary component can be more resistant to, for example, damage (e.g., fracturing, failure) when used during a medical procedure and/or during a manufacture process than if the reinforcement component were not present. In some embodiments, the optical waveguide of a side-fire member can be fused to a capillary component of the side-fire member such that the side-fire member may be relatively resistant to, for example, damage during use and/or manufacture. In some embodiments, a relatively hard coating (e.g., a diamond-like coating, a magnesium-based coating such as a magnesium oxide coating or a magnesium fluoride coating) can also be disposed around at least a portion of the side-fire member so that the distal end portion may be relatively resistant to, for example, damage during use and/or manufacture. In some embodiments, a side-fire member of a side-fire system can be configured so that the optical waveguide of the side-fire member is not disposed within a capillary component. In some embodiments, at least some features of the distal end portion of the side-fire member can be configured so that they are relatively simple to manufacture.

In some embodiments, the devices and methods described herein can be used in treating symptoms related to, for example, an enlarged prostate gland, a condition known as Benign Prostatic Hyperplasia (BPH). BPH is a common condition in which the prostate becomes enlarged with aging. The prostate is a gland that is part of the male reproductive system. The prostate gland includes two lobes that are enclosed by an outer, layer of tissue and is located below the bladder and surrounding the urethra, the canal through which urine passes out of the body. Prostate growth can occur in different types of tissue and can affect men differently. As a result of these differences, treatment varies in each case. No cure for BPH exists, and once the prostate begins to enlarge, it often continues, unless medical treatment is initiated.

Patients who develop symptoms associated with BPH generally require some form of treatment. When the prostate gland is mildly enlarged, research studies indicate that early treatment may not be needed because the symptoms can clear up without treatment in as many as one-third of cases. Instead of immediate treatment, regular checkups are recommended. Only if the condition presents a health risk, or the symptoms result in major discomfort or inconvenience to the patient, is treatment generally recommended. Current forms of treatment include drug treatment, minimally-invasive therapy, and surgical treatment. Drug treatment is not effective in all cases and a number of medical procedures have been developed to relieve BPH symptoms that are less invasive than conventional surgery.

While drug treatments and minimally-invasive procedures have proven helpful for some patients, many doctors still recommend surgical removal of the enlarged part of the prostate as the most appropriate long-term solution for patients with BPH. For the majority of cases that require surgery, a procedure known as Transurethral Resection of the Prostate (TURP) is used to relieve BPH symptoms. In this procedure, the medical practitioner inserts an instrument called a resectoscope into and through the urethra to remove the obstructing tissue. The resectoscope also provides irrigating fluids that carry away the removed tissue to the bladder.

More recently, laser-based surgical procedures employing side-fire systems that include relatively high-power laser sources have been used to remove obstructing prostate tissue. In these procedures, a doctor passes the side-fire member of the side-fire system through the urethra using a cystoscope, a specialized endoscope with a small camera on the end, and then delivers multiple bursts of laser energy within an optical waveguide of the wide-fire member to destroy some of the enlarged prostate tissue and to shrink the size of the prostate. Patients who undergo laser surgery usually do not require overnight hospitalization, and in most cases, the catheter is removed the same day or the morning following the procedure. Generally, less bleeding occurs with laser surgery and recovery times tend to be shorter than those of traditional procedures such as TURP surgery.

A common laser-based surgical procedure is Holmium Laser Enucleation of the Prostate (HoLEP). In this procedure, a holmium:YAG (Ho:YAG) laser is used to remove obstructive prostate tissue. The Ho:YAG surgical laser is a solid-state, pulsed laser that emits light at a wavelength of approximately 2100 nanometers (nm). This wavelength of light is particularly useful for tissue ablation as it is strongly absorbed by water. An advantage of Ho:YAG lasers is that they can be used for both tissue cutting and for coagulation. Another common laser surgery procedure is Holmium Laser Ablation of the Prostate (HoLAP), where a Ho:YAG laser is used to vaporize obstructive prostate tissue. The decision whether to use HoLAP or HoLEP is based primarily on the size of the prostate. For example, ablation may be preferred when the prostate is smaller than 60 cubic centimeters (cc). Laser-based surgical procedures, such as HoLAP and HoLEP, are often preferred because they produce similar results to those obtained from TURP surgery while having fewer complications and requiring shorter hospital stay, shorter catheterization time, and shorter recovery time.

It is noted that, as used in this written description and the appended claims, the singular forms "a," "an" and "the" include plural referents unless the context clearly dictates otherwise. Thus, for example, the term "a wavelength" is intended to mean a single wavelength or a combination of wavelengths. Furthermore, the words "proximal" and "distal" refer to direction closer to and away from, respectively, an operator (e.g., a medical practitioner, a medical practitioner, a nurse, a technician, etc.) who would insert the medical device into the patient. Thus, for example, the side-fire member end inserted inside a patient's body would be the distal end of the side-fire member, while the side-fire member end outside a patient's body would be the proximal end of the side-fire member.

FIG. 1 is a schematic diagram of a side-fire system 110, according to an embodiment. The side-fire system 110 can include a laser source 111, an optical coupler 112, a side-fire member 114, and a distal end portion 116 of the side-fire member 114. The side-fire system 110 also includes a suitable catheter or endoscope 115 through which the side-fire member 114 can be inserted into a patient's body.

The laser source 111 can be configured to generate laser energy that can be propagated within the side-fire member 114, for example, during a surgical procedure. The laser source 111 can include, for example, a Ho:YAG laser source, a neodymium-doped:YAG (Nd:YAG) laser source, a semiconductor laser diode, and/or a laser source employing a non-linear element (e.g., a laser source that includes a potassium-titanyl phosphate crystal (KTP) laser source). In some embodiments, more than one laser source can be used during a surgical procedure.

In some embodiments, the laser source 111 can also have a control module (not shown) configured to control (e.g., to set, to modify) a timing, a wavelength, and/or a power of Laser energy emitted from the laser source 111. In some embodiments, the control module can also be configured to perform various functions such as laser selection, filtering, temperature compensation, and/or Q-switching. The control module can be a hardware-based control module and/or a software-based control module that can include, for example, a processor and/or a memory.

The side-fire member 114 can be coupled to the laser source 111 through the optical coupler 112. The optical coupler 112 can be, for example, a Sub-Miniature A (SMA) connector. The proximal end of the side-fire member 114 can be configured to receive laser energy from the laser source 111, and the distal end of the side-fire member 114 can be configured to output the laser energy 120 through the distal end portion 116 of the side-fire member 114. The side-fire member 114 can include an optical waveguide (not shown in FIG. 1) that has, for example, a fiber core, one or more cladding layers disposed around the fiber core, and/or a buffer layer disposed around the cladding layer(s). A jacket can also be disposed around the optical waveguide (e.g., around a buffer layer of the optical waveguide). In some embodiments, the buffer layer can function as a cladding layer.

In some embodiments, the fiber core can be made of a suitable material for the transmission of laser energy from the laser source 111. In some embodiments, for example, the fiber core can be made of silica with a low hydroxyl (OH⁻) ion residual concentration. Laser energy wavelengths ranging from about 500 nm to about 2100 nm can be propagated within the fiber core during a surgical procedure. An example of low hydroxyl (low-OH) fibers used in medical devices is described in U.S. Pat. No. 7,169,140 to Kume, the disclosure of which is incorporated herein by reference in its entirety. The fiber core can be a multi-mode fiber core and can have a step or graded index profile. The fiber core can also be doped with a dopant (e.g., an amplifying dopant).

The cladding can be a single or a double cladding that can be made of a hard polymer or silica. The buffer (which can function as a cladding layer) can be made of a hard polymer or acrylate, for example. When the optical fiber includes a jacket, the jacket can be made of Tefzel®, for example, or can be made of other polymer-based substances.

The distal end portion 116 of the side-fire member 114 can include one or more surfaces that can individually or collectively operate to redirect laser energy in a direction non-parallel (e.g., a lateral direction) to a longitudinal axis or a centerline of the distal end of the fiber core. Such a surface can be an angled surface (not shown in FIG. 1) defined by, for example, the fiber core, one or more cladding layers about the fiber core, and/or a buffer layer. The angled surface can be non-normal to a longitudinal axis (or centerline) of a distal end portion 116 of the side-fire member 114. In some embodiments, the angled surface can be, for example, a reflecting member with a multilayer dielectric coating on an angled surface. More details related to an example of a reflecting member are set forth in co-pending U.S. patent application Ser. No. 61/054,280, entitled, "Side-Firing Laser Fiber with Protective Tip and Related Methods," filed May 19, 2008, and in co-pending U.S. patent application Ser. No. 12/467,730, entitled, "Side-Firing Laser Fiber with Protective Tip and Related Methods," filed May 18, 2009, and published as U.S. Patent Application Publication No. US 2009/0287199 A1, both of which are incorporated herein by reference in their entireties.

As described above, the distal end portion 116 of the side-fire member 114 can be configured so that it is relatively resistant to damage when used during a medical procedure and/or during manufacture of the distal end portion 116 of the side fire member 114. More details related to the various configurations of the distal end portion 116 of the side-fire member 114 (which can be combined in various combinations) are described in connection with FIG. 2 through FIG. 9.

In some embodiments, the endoscope 115 can define one or more lumens (also can be referred to as working channels). In some embodiments, the endoscope 115 can include a single lumen that can receive therethrough various components such as the side-fire member 114. The endoscope 115 can have a proximal end configured to receive the distal end portion 116 of the side-fire member 114 and a distal end configured to be inserted into a patient's body for positioning the distal end portion 116 of the side-fire member 114 in an appropriate location for a laser-based surgical procedure. For example, to relieve symptoms associated with BPH, the endoscope 115 can be used to place the distal end portion 116 at or near the enlarged portion of the prostate gland. The endoscope 115 can include an elongate portion that can be sufficiently flexible (or rigid) to allow the elongate portion of the side-fire member 114 to be maneuvered within the body.

The endoscope 115 can also be configured to receive various medical devices or tools through one or more lumens of the endoscope 115, such as, for example, irrigation and/or suction devices, forceps, drills, snares, needles, etc. An example of such an endoscope with multiple lumens is described in U.S. Pat. No. 6,296,608 to Daniels et al., the disclosure of which is incorporated herein by reference in its entirety. In some embodiments, a fluid channel (not shown) is defined by the endoscope 115 and coupled at a proximal end to a fluid source (not shown). The fluid channel can be used to irrigate an interior of the patient's body during a laser-based surgical procedure. In some embodiments, an eyepiece (not shown) can be coupled to a proximal end portion of the endoscope 115, for example, and coupled to a proximal end portion of an optical fiber that can be disposed within a lumen of the endoscope 115. Such an embodiment allows a medical practitioner to view the interior of a patient's body through the eyepiece.

Figure 2:
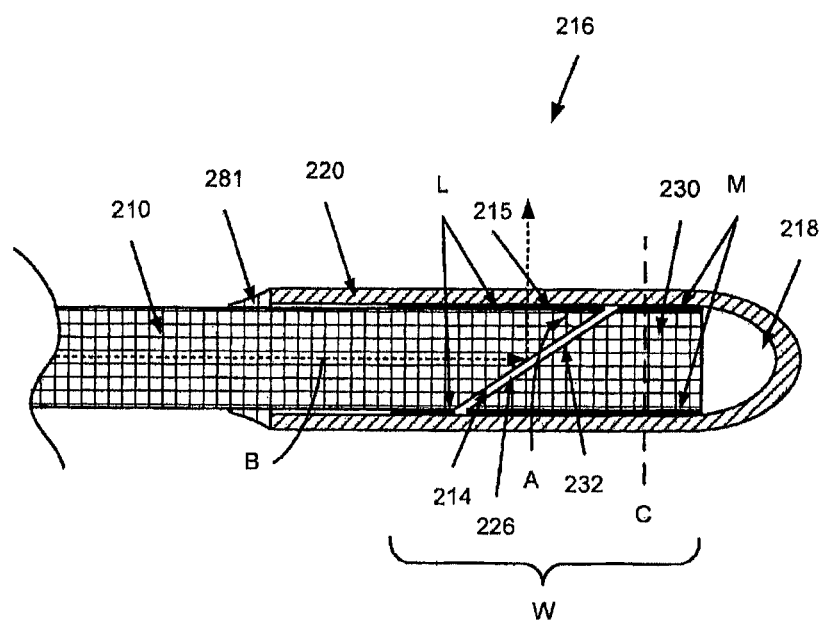
FIG. 2 is a schematic diagram that illustrates a side cross-sectional view of a distal end portion of a side-fire member that has a reinforcement component, according to an embodiment.

FIG. 2 is a schematic diagram that illustrates a side cross-sectional view of a distal end portion 216 of a side-fire member that has a reinforcement component 230, according to an embodiment. As shown in FIG. 2, a distal end portion of an optical waveguide 210 and the reinforcement component 230 are disposed inside of a capillary component 220. Specifically, an outer surface of the optical waveguide 210 and an outer surface of the reinforcement component 230 are coupled to (e.g., heat-fused to, adhesively coupled to) an inner surface of the capillary component 220.

As shown in FIG. 2, laser energy B is propagated along a longitudinal axis (or centerline) of the optical waveguide 210 of the distal end portion 216 and at least a portion of laser energy B is redirected by an interface defined by an angled surface 214 and a fluid (e.g., a gas, a liquid) within a gap 226. In some embodiments, the fluid can be air or a different fluid. As shown in FIG. 2, the gap 226 is defined by the capillary component 220, the angled surface 214, and the surface 232 of the reinforcement component 230. The portion of the laser energy B that is redirected is transmitted through a portion of the capillary component 220. In other words, the laser energy B is transmitted within one or more optical paths along the longitudinal axis (or centerline) of the optical waveguide 210, and the laser energy B is redirected and transmitted within one or more optical paths that intersects the capillary component 220. In some embodiments, the optical path(s) can include multiple segments. Although not shown, the optical waveguide 210 can have, for example, a fiber core, one or more cladding layers around the fiber core, and/or a buffer layer. Although not shown in FIG. 2, a jacket layer can be disposed around a portion of the optical waveguide 210 proximal to the capillary component 220.

In some embodiments, an angle A can be between 20 and 85 degrees (e.g., 40 degrees). The angle A can be referred to as an angle of the angled surface 214. In some embodiments, the angle A can be defined so that laser energy propagated within the optical waveguide 210 (such as laser energy B) will be redirected in substantially a lateral direction relative to a longitudinal axis or centerline of the optical waveguide 210. At least a portion of laser energy B will be redirected at an interface defined by the angled surface 214 and air in the gap 226 when the angle A is at least approximately 38 degrees.

The reinforcement component 230 is coupled to the inner surface of the capillary component 220 distal to the optical waveguide 210 to physically reinforce portions of the capillary component 220 distal to the optical waveguide 210. Specifically, the reinforcement component 230 can be coupled to the capillary component 220 so that the capillary component 220 may be relatively resistant to damage (e.g., fracturing) when shockwaves (e.g., acoustic shockwaves) impinge upon the capillary component 220 from collapsing gas bubbles that may form during use of the distal end portion 216 of the side-fire member. The gas bubbles may be formed in a fluid medium outside of the distal end portion 216 in response to heat from pulsing laser energy propagated through the optical waveguide 210 and laterally out of the distal end portion 216.

In some embodiments, the reinforcement component 230 can be coupled to the capillary component 220 such that fracturing of the capillary component 220 along a portion of the capillary component 220 substantially aligned with the angled surface 214 can be substantially prevented. In other words, without the reinforcement component 230 being coupled to an inner surface of the capillary component 220, the capillary component 220 may fracture along a portion of the capillary component 220 aligned along or substantially aligned along the angled surface 214. When the reinforcement component 230 is coupled to the inner surface of the capillary component 220 one or more mechanical properties (e.g., the stiffness, the flexibility) of the distal end portion 216 of the side-fire member can be relatively uniform along a longitudinal axis of the distal end portion 216. The mechanical properties of the distal end portion 216 of the side-fire member can be relatively uniform, in particular, within region W, which is the region within which the optical waveguide 210 and the reinforcement component 230 are heat-fused to the capillary component 220. As shown in FIG. 2, the angled surface 214 is disposed within the region W.

In some embodiments, because the reinforcement component 230 is coupled to the capillary component 220, the portions of the capillary component 220 distal and proximal to the angled surface 214 will have substantially the same mechanical properties such as stiffness, flexibility, and so forth. In particular, the stiffness of the portion of the capillary component 220 proximate to heat-fused region L and the portion of the capillary component proximate to heat-fused region M will have substantially the same mechanical properties.

As shown in FIG. 2, an outer surface of the reinforcement component 230 is heat-fused (shown at M) to an inner surface of the capillary component 220. An outer surface of the optical waveguide 210 is heat-fused (shown at L) to an inner surface of the capillary component 220. In some embodiments, an entire circumference of a cross-sectional portion of the outer surface of the optical waveguide 210 can be heat-fused to at least a portion of the inner surface of the capillary component 220. In some embodiments, an entire circumference of a cross-sectional portion of the reinforcement component is heat-fused to at least the first portion of the inner surface of the capillary component. The reinforcement component 230 can be coupled to the capillary component 220 so that, for example, a mechanical strength of the distal end portion 216 proximal to the angled surface 214 will be substantially the same as the mechanical strength of the distal end portion 216 distal to the angled surface 214. If the reinforcement component 230 were not coupled to a portion of the capillary component 220 distal to the angled surface 214 (as shown in FIG. 2), the capillary component 220 may be, for example, more susceptible to flexing and breakage during use than the portion of the capillary component 220 proximal to the angled surface 214. The portion of the capillary component 220 proximal to the angled surface 214 can be relatively, for example, resistant to flexing and breakage because the portion of the capillary component 220 proximal to the angled surface 214 is coupled to the optical waveguide 210.

As shown in FIG. 2, the entire circumferential surface area of the reinforcement component 230 (shown as heat-fused region M) is heat-fused to the inner surface of the capillary component 220. In some embodiments, less than the entire circumferential surface area of the reinforcement component 230 can be heat-fused to the inner surface of the capillary component 220. For example, in some embodiments, a portion (e.g., a cross-sectional portion) of the outer surface of the reinforcement component that is proximal to a plane C, which is substantially normal to a longitudinal axis (or centerline) of the optical waveguide 210, can be heat-fused to the capillary component 220. In some embodiments, multiple locations along the outer surface of the reinforcement component 230 can be heat-fused to the inner surface of the capillary component 220. For example, a portion of the outer surface of the reinforcement component 230 near the proximal end of the doped silica component 220 and/or a portion of the outer surface 215 near the angled surface 217 can be heat fused to the inner surface of the doped silica component 220. In some embodiments, two or more cross-sectional portions of the outer surface 215 can be heat-fused to the doped silica component 220.

In some embodiments, one or more portions of the reinforcement component 230 can be adhesively coupled to the capillary component 220. For example, a portion of the reinforcement component 230 that is not heat-fused to the capillary component 220 can be adhesively coupled (e.g., adhesively coupled using an epoxy) to the capillary component 220. In some embodiments, at least a portion of the reinforcement component 230 may be adhesively coupled to the capillary component 220 without any portion of the reinforcement component 230 being heat-fused to the capillary component 220. In some embodiments, one or more portions of the reinforcement component 230 can have dimensions defined so that the reinforcement component 230 can be press fit inside of the capillary component 220 (with or without being adhesively and/or heat-fused to the capillary component 220).

As shown in FIG. 2, an enclosure 218 is defined by an inner surface of the capillary component 220 and the distal end of the reinforcement component 230. In some embodiments, the distal end portion 216 may not have an enclosure such as enclosure 218. In some embodiments, the enclosure 218 may be filled with a fluid that is the same or substantially the same as that in the gap 226. In other words, the capillary component 220 and/or the reinforcement component 230 can be defined so that at least a distal end portion of the reinforcement component 230 is in contact with an inner surface of the capillary component 220. In some embodiments, the reinforcement component 230 does not have a flat distal end surface such as that shown in FIG. 2. In some embodiments, the enclosure 218 is filled with a filler material such as an adhesive (e.g., an epoxy, a polymer-based material).

Although not shown, in some embodiments, the capillary component 220 can be defined so that the capillary component 220 has, for example, a tubular shape that does not define a cap. In such embodiments, a distal end of the reinforcement component 230 can be in fluid communication with an environment outside of the capillary component 220.

In some embodiments, a proximal end surface 232 of the reinforcement component 230 can be a non-zero distance from the angles surface 214. In other words, the gap 226 can have a non-zero width. In some embodiments, the proximal end surface 232 of the reinforcement component 230 can be relatively close to the angled surface 214. For example, the proximal end surface 232 of the reinforcement component 230 may separated from the angled surface 214 of the optical waveguide 210 by less than an inch (e.g., by a hundredth of an inch). In some embodiments, a center portion of the proximal end surface 232 of the reinforcement component 230 may separated from a center portion of the angled surface 214 of the optical waveguide 210 by less than a hundredth of an inch. In some embodiments, the width of the gap 226 can be maintained by one or more spacers (not shown) disposed between the reinforcement component 230 and the optical waveguide 210.

In some embodiments, the gap 226 between the distal end surface of the optical waveguide 210 and a proximal end surface 232 of the reinforcement component 230 may be fluidically isolated from the enclosure 218. As shown in FIG. 2, the gap 226 and the enclosure 218 can be isolated by the weld region M. Although not shown, in some embodiments, the gap 226 between the distal end surface of the optical waveguide 210 and a proximal end surface 232 of the reinforcement component is not be fluidically isolated from the enclosure 218. In such embodiments, the gap 226 may be in fluid communication with the enclosure 218 via an opening through the weld region M. In such embodiments, the weld region M does not entirely surround (i.e., may not be contiguous around) the reinforcement component 230.

As shown in FIG. 2, a plane defined by the proximal end surface 232 of the reinforcement component 230 is substantially parallel to a plane defined by the angled surface 214 of the optical waveguide 210. In some embodiments, the plane defined by the proximal end surface 232 may be non-parallel to the plane defined by the angled surface 214 of the optical waveguide 210.

In some embodiments, the reinforcement component 230 can have a different shape than that shown in FIG. 2. For example, the reinforcement component 230 can have a tubular shape that is oriented within the capillary component 220 so that the gap 226 is in fluid communication with the enclosure via a bore of the reinforcement component 230. In some embodiments, the reinforcement component 230 can have one or more curved surfaces (e.g., concave surfaces, convex surfaces) and/or flat surface (that are not shown). For example, a distal end of the reinforcement component 230 can have a concave surface configured to be in contact with and/or coupled to at least a portion of an inner surface of the capillary component 220. In some embodiments, the reinforcement component 230 can have a shape that conforms to that of the capillary component 220. For example, if the capillary component 220 has a shape that tapers (not shown) from a proximal end to a distal end (or vice versa), the reinforcement component 230 can have a shape that conforms to that of the capillary component 220 so that the reinforcement component 230 can be heat-fused to an inner surface of the capillary component 220.

Although not shown, in some embodiments, the multiple reinforcement components can be coupled to an inner surface of the capillary component 220. In such embodiments, the reinforcement components can be separated by a gap or can be in contact with one another. Although not shown, in some embodiments, the reinforcement component 230 can be made from multiple separate components that are in contact with one another or coupled together (e.g., heat-fused together).

In some embodiments, the reinforcement component 230 can have one or more properties (e.g., mechanical properties) that are substantially the same or different from the properties of the optical waveguide 210 and/or capillary component 220. For example, in some embodiments, the reinforcement component 230 can have a hardness that substantially corresponds to a hardness of at least a portion of the capillary component 220 or a hardness of at least a portion of the optical waveguide 210 such as a fiber core (not shown) of the optical waveguide 210, a cladding layer (not shown) of the optical waveguide 210, and/or so forth. In some embodiments, the reinforcement component 230 can have a coefficient of thermal expansion substantially corresponding to a coefficient of thermal expansion of at least a portion of the optical waveguide 210 or at least a portion of the capillary component 220.

Although not shown, in some embodiments, the proximal end surface of the reinforcement component 230 can be made of a reflective material and/or can be coupled to a reflective material. The reflective material can be used to reflect, for example, a portion of the laser energy B that is not redirected by the interface defined by the angled surface 214 and the gap 226. In other words, a portion of the laser energy B that passes through the gap 226 can be redirected by the reflective material associated with the reinforcement component 230.

In some embodiments, the reinforcement component 230 can be made of a silica-based material that substantially corresponds with a silica-based material of at least one of a fiber core of the optical waveguide 210 (e.g., a cladding of the optical waveguide). For example, the reinforcement component 230 can be made of a pure (or substantially pure) silica ($SiO_2$) material. For example, the optical waveguide 210 can be made of a fluorine-doped silica material. As shown in FIG. 2, the reinforcement component 230 has an outer diameter that is the same as (or substantially the same as) an outer diameter of the optical waveguide 210.

In some embodiments, the index of refraction of any portion of the distal end portion 216 of a side-fire member (e.g., the capillary component 220, the reinforcement member 230) can be defined at least in part by a doping concentration of a dopant (e.g., a fluorine dopant, a chlorine dopant, a rare-earth dopant, a germanium dopant, an alkali metal dopant, an alkali metal oxide dopant, etc.). The optical waveguide 210, the capillary component 220, and/or the reinforcement component 230 can have the same or different doping.

Although not shown, in some embodiments, multiple capillary components can be disposed around the angled surface 214 of the optical waveguide 210 and/or the reinforcement component 230. Accordingly, the portion of the laser energy B redirected by interface defined by the angled surface 214 and the fluid in the gap 226 can be transmitted through one or more of the capillary components. More details related to side-fire systems that include multiple capillary components are described in connection with U.S. Provisional Application No. 61/262,404, filed on Nov. 18, 2009, and entitled, "Methods and Apparatus related to a Distal end of a Side-Fire Optical Fiber Having Multiple Capillary Components," and U.S. Nonprovisional Application Ser. No. 12/947,365, filed on Nov. 16, 2010, and entitled, "Methods and Apparatus related to a Distal end of a Side-Fire Optical Fiber Having Multiple Capillary Components," both of which are incorporated herein by reference in their entireties.

Although not shown, in some embodiments, an outer cover (e.g., a metallic cap, a polymer-based cap) can be disposed outside of the capillary component 220. The outer cover can be substantially opaque to a spectral region of electromagnetic radiation associated with the laser energy B propagated within the optical waveguide 210. In some embodiments, the outer cover can have a transmissive portion (e.g., a window or an opening) through which redirected laser energy (such as a portion of laser energy B) can be transmitted.

As shown in FIG. 2, an adhesive 281 (such as an epoxy) is used to couple a proximal end of the capillary component 220 to an outer surface of the optical waveguide 210. Although not shown, in some embodiments, the proximal end of the capillary component 220 is not coupled to an outer surface of the optical waveguide 210 with an adhesive.

Figure 3A:
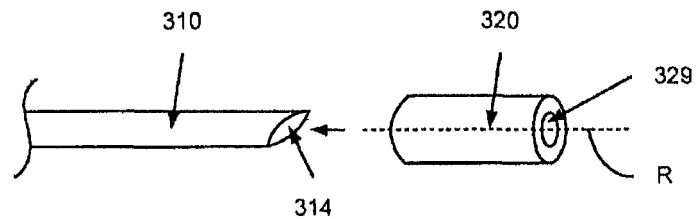
FIGS. 3A through 3D collectively illustrate a method for producing a side-fire member that has a reinforcement component, according to an embodiment.
Figure 3B:
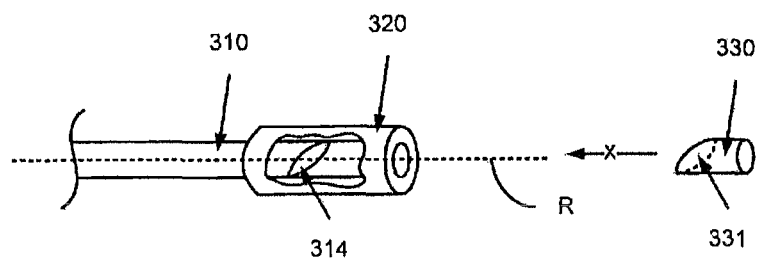
Figure 3C:
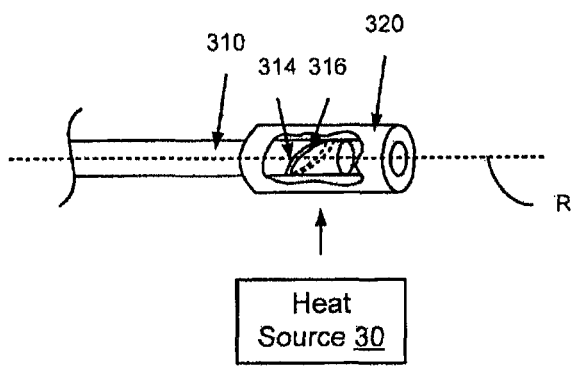
Figure 3D:
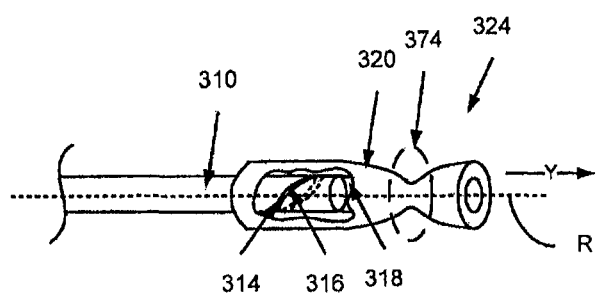

FIGS. 3A through 3D collectively illustrate a method for producing a side-fire member that has a reinforcement component, according to an embodiment. FIG. 3A is a schematic diagram that illustrates a capillary component 320 and an optical waveguide 310 before the capillary component 320 is disposed over the optical waveguide 310, according to an embodiment. FIG. 3B is a schematic diagram that illustrates insertion of a reinforcement component 330 into the capillary component 320 after the capillary component 320 is disposed over the optical waveguide 310, according to an embodiment. FIG. 3C is a schematic diagram that illustrates heating of the distal end portion of the side-fire member when the reinforcement component 320 and the optical waveguide 310 are disposed within the capillary component 320, according to an embodiment. FIG. 3D is a schematic diagram that illustrates a distal end 324 of the capillary component 320 being heated and pulled, according to an embodiment.

As shown in FIG. 3A, an angled surface 314 is defined at a distal end of the optical waveguide 310 before the capillary component 320 is disposed over the optical waveguide 310. The angled surface 314 can be initially cut using, for example, a laser energy cutting instrument and/or a mechanical cutting instrument before and/or after at least a portion of a jacket (not shown) around the optical waveguide 310 has been removed. After the angled surface 314 has been initially cut, the angled surface 314 can be polished using, for example, a mechanical polishing instrument.

As shown in FIG. 3A, the capillary component 320 has a bore 329 (e.g., a lumen) along a longitudinal axis (or centerline) X of the capillary component 320. The bore 329 of the capillary component 320 is in fluid communication with an opening at each end (along the longitudinal axis (or centerline) X) of the capillary component 320. The capillary component 320 can be cut from a length of a tubular (e.g., cylindrical) pre-form (not shown). The capillary component 320 component can be cut from the pre-form using, for example, a laser energy cutting instrument or a mechanical cutting instrument. The pre-form can be cut along a plane that is substantially normal to a longitudinal axis (or centerline) X of the pre-form.

In some embodiments, the capillary component 320 can be uniformly or non-uniformly doped with, for example, fluorine and/or another suitable dopant. In some embodiments, the capillary component 320 can be between 30 millimeters to 10 centimeters long. In some embodiments, the doped-silica tubular pre-form can have a doping concentration that is higher near an inner surface that defines the bore than at an outer surface of the pre-form (or vice versa).

In some embodiments, the size of the bore 329 can be increased before being disposed over the optical waveguide 310. In some embodiments, the size of the bore 329 can be increased by removing a portion of a wall defining the bore 329 with, for example, a reaming device. An inner diameter of the bore 329 can be defined so that it is, for example, at least a few micrometers larger than an outer diameter of the optical waveguide 310.

FIG. 3B is a schematic diagram that illustrates insertion of a reinforcement component 330 into the capillary component 320 after the capillary component 320 is disposed over the optical waveguide 310, according to an embodiment. As shown in FIG. 3B, the reinforcement component 330 is inserted in direction X into the capillary component 320. A proximal surface 331 of the reinforcement component 330 can be oriented so that it is substantially parallel to the angled surface 314 defined by the optical waveguide 310 when the reinforcement component 330 is being inserted into the capillary component 320.

The reinforcement component 330 can be inserted into the capillary component 320 so that a gap 316 (shown in FIG. 3C) is between the surface 331 of the reinforcement component 330 and the angled surface 314. Although not shown, in some embodiments, the size of the gap 316 can be defined by a spacer inserted between the surface 331 and the angled surface 314. In some embodiments, the gap 316 can be defined using an instrument configured to insert the reinforcement component 330 a specified distance into the capillary component 320. In some embodiments, the reinforcement component 330 and/or the capillary component 320 can have one or more markings (not shown) that can be used to determine a distance that the surface 331 has been inserted into the capillary component 320.

As shown in FIG. 3C, after the reinforcement component 330 has been inserted into the capillary component 320, at least a portion of an outer surface of the optical waveguide 310 and at least a portion of an outer surface of the reinforcement component 330 can be heat-fused to at least a portion of an inner surface of the capillary component 330. In some embodiments, the capillary component 320 and optical waveguide 310 can be heated using, for example, a heat source 30 (e.g., a torch, an electrical heating element, a laser source) until the capillary component 320 is fused to the optical waveguide 310 and the reinforcement component 330. The capillary component 320, the optical waveguide 310, and the reinforcement component 330 can be rotated about a longitudinal axis (or centerline) R of the optical waveguide 310 while being heated.

As shown in FIG. 3D, the distal end 324 is being heated in a zone 374 while being pulled in direction Y until an enclosure 318 is formed. In other words, a force in direction Y (away from the angled surface 314) is applied on the distal end 324 while the zone 374 is being heated. The capillary component 320 can be heated until the capillary component 320 softens and can be pulled. As the zone 374 of the capillary component 320 is heated and the distal end 324 of the capillary component 320 is pulled, the capillary component 320 plastically deforms until at least a portion of the distal end 324 is separated from the capillary component 320 so that the capillary component 320 defines a cap (such as that shown in FIG. 2). Although not shown, in some embodiments, the capillary component 320 can be heated so that at least a portion of the capillary component 320 is heat-fused to at least a portion of the distal end of the reinforcement component 330.

In some embodiments, the heating and/or pulling discussed in connection with FIG. 3D are not performed coincidentally. For example, a portion of the distal end 324 can be heated before the distal end 324 is pulled. In some embodiments, the optical waveguide 310, the capillary component 320, and the reinforcement component 330 can be rotated, for example, around the longitudinal axis (or centerline) R while being heated and/or pulled. In some embodiments, the heating associated with FIG. 3B (during fusing) and the heating associated with FIG. 3D can be performed using the same heat source (e.g., heat source 30) and/or can be performed within the same heating cycle. In some embodiments, the heating associated with FIG. 3B and the heating associated with FIG. 3D can be performed separately (e.g., different space and time) using different heating sources.

Although not shown, in some embodiments, an outer cover (e.g., a metal cover, a plastic cover, a hard coating) can be disposed over and coupled to the capillary component 320. In some embodiments, at least a portion of the outer cover that is transmissive to laser energy can be disposed within (e.g., intersects) an optical path of the laser energy redirected at an interface defined at least in part by the angled surface 314.

In some embodiments, the reinforcement component 330 can be inserted into the capillary component 320 and/or heat-fused within the capillary component 320 using a method different than that shown in FIGS. 3A through 3D. For example, in some embodiments, the reinforcement component 330 can be inserted into the capillary component 320 before the capillary component 320 is moved over the distal end portion of the optical waveguide 310. In such embodiments, the reinforcement component 330 may or may not be heat-fused to the capillary component 320 before the capillary component is moved over the distal end portion of the optical waveguide 310. In some embodiments, the waveguide 310 can be heat-fused to the capillary component 320 before the reinforcement component 330 is inserted into the capillary component 320. In such embodiments, the heat-fusing of the optical waveguide 310 to the capillary component 320 and the heat-fusing of the reinforcement component 330 to the capillary component 320 can be performed during substantially different time periods. In some embodiments, at least a portion of the reinforcement component 330 can be adhesively coupled to the capillary component 320.

In some embodiments, the capillary component 320 can define a cap before being disposed over the waveguide 310. In such embodiments, the reinforcement component 330 can be inserted into the capillary component 320 (through an opening opposite that of the cap end of the capillary component 320) before the capillary component 320 is moved over the distal end portion of the optical waveguide 310. Also, in such embodiment, the heating and pulling shown in FIG. 3D is not performed.

Figure 4:
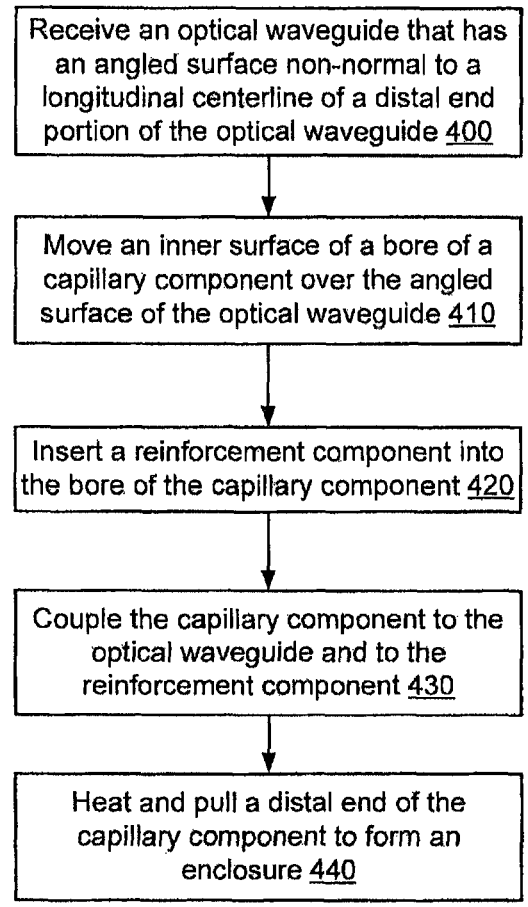
FIG. 4 is a flowchart that illustrates a method for manufacturing a side-fire member that has a reinforcement component, according to an embodiment.

FIG. 4 is a flowchart that illustrates a method for manufacturing a side-fire member that has a reinforcement component, according to an embodiment. As shown in FIG. 4, an optical waveguide that has an angled surface non-normal to a longitudinal centerline of a distal end portion of the optical waveguide is received, at 400. The angled surface can be defined using a cleaving and polishing process.

An inner surface of a bore of a capillary component is moved over the angled surface of the optical waveguide, at 410. The capillary, component may or may not be doped with a dopant such as fluorine. In some embodiments, the capillary component can be cut from a preform.

A reinforcement component is inserted into the bore of the capillary component, at 420. In some embodiments, the reinforcement component can be inserted into the capillary component with a specified orientation with respect to the angled surface of the optical waveguide. In some embodiments, the orientation of the reinforcement component with respect to the capillary component and/or the angled surface can be modified after the reinforcement component is inserted into the capillary component.

The capillary component is coupled to the optical waveguide and to the reinforcement component, at 430. In some embodiments, an outer surface of the optical waveguide and an outer surface of the reinforcement component can be heat-fused to an inner surface of the capillary component. In some embodiments, an outer surface of the optical waveguide and/or an outer surface of the reinforcement component can be coupled to an inner surface of the capillary component using, for example, an adhesive.

A distal end portion of the capillary component can be heated and/or pulled to form an enclosure, at 440. In some embodiments, the enclosure can be defined by at least a portion of the reinforcement component and the capillary component.

Figure 5:
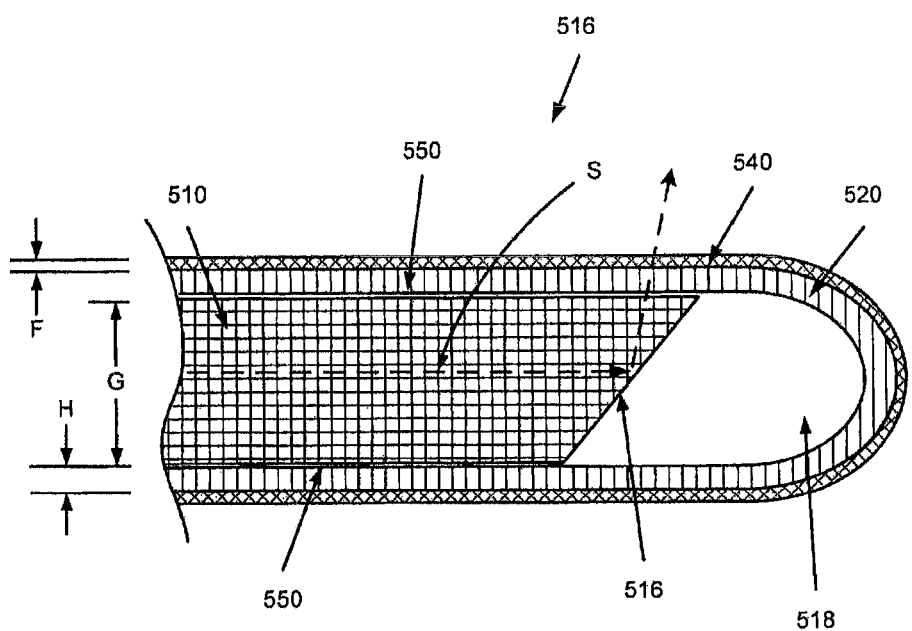
FIG. 5 is a schematic diagram that illustrates a side cross-sectional view of a coating disposed outside of a capillary component of a side-fire member, according to an embodiment.

FIG. 5 is a schematic diagram that illustrates a side cross-sectional view of a coating 540 disposed outside of a capillary component 520 of a side-fire member, according to an embodiment. The coating 540 is defined so that the coating 540 will protect the capillary component 520. In some embodiments, the coating 540 can be a relatively hard, optically clear coating configured to, for example, reduce the rate of pitting as the side-fire member is used.

As shown in FIG. 5, the coating 540 is disposed outside of a capillary component 520 that is coupled (e.g., heat-fused) to a distal end portion of an optical waveguide 510. The optical waveguide 510 has an angled surface 516 that defines at least a portion of an interface configured to redirect at least a portion of laser energy S propagated within the optical waveguide 510.

In some embodiments, the coating 540 can be a relatively hard material that is also configured to allow a specified range of electromagnetic radiation to pass through. In some embodiments, the material can have a hardness substantially the same as, greater than, or less than a material used to make the capillary component 520. In some embodiments, the coating 540 can be, for example, a diamond-like material, a magnesium oxide material, a magnesium fluoride material, and/or so forth. In some embodiments, the coating 540 can be a material used for optical anti-reflection coatings on, for example, a lens.

In some embodiments, the coating 540 may be either a monolayer or a multilayer coating. For example, multiple layers of a material can be used to define the coating 540. In some embodiments, multiple layers made of different materials can be used to define the coating 540. For example, a first portion (e.g., a first layer) of the coating 540 can be defined by a diamond-like material and a second portion (e.g., a second layer) of the coating 540 can be defined by a magnesium fluoride material. In some embodiments, the first portion can be disposed inside of (e.g., interior to) the second portion. In some embodiments, the first portion can be disposed distal to the second portion. In some embodiments, the combined optical and/or mechanical properties may be desirable. For example, a first portion of the coating 540 may have optical and/or mechanical properties that may complement, increase, and/or diminish the optical and/or mechanical properties of a second portion of the coating 540.

In some embodiments a fiber core (not shown) of the optical waveguide 510 of the side-fire member can have an outer diameter, for example, between approximately 20 micrometers (μm) to 1200 μm. A cladding layer (not shown) of the optical waveguide 510 can have a thickness of between, for example, approximately 5 μm to 120 μm. In some embodiments, the outer diameter G of the optical waveguide 510 can be more than 1 to 1.3 times greater than the outer diameter of the fiber core of the optical waveguide 510. The capillary component 520 can have a thickness H of between, for example, approximately 5 μm to several millimeters. The coating 540 can have a thickness F of several micrometers to several millimeters.

Figure 6:
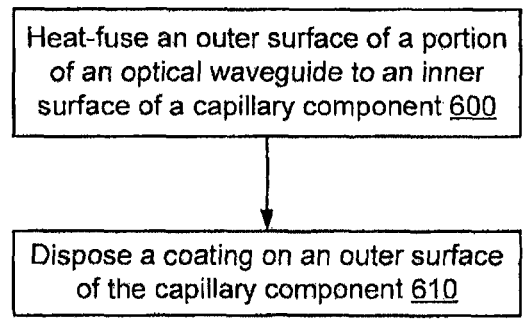
FIG. 6 is a flowchart that illustrates a method for producing a distal end portion of a side-fire member that has a coating, according to an embodiment.

FIG. 6 is a flowchart that illustrates a method for producing a distal end portion of a side-fire member that has a coating, according to an embodiment. As shown in FIG. 6, an outer surface of a portion of an optical waveguide is heat-fused to an inner surface of a capillary component, at 600. In some embodiments, at least a portion of the optical waveguide can be adhesively coupled to the capillary component.

A coating is disposed on an outer surface of the capillary component, at 610. In some embodiments, the coating can be disposed on the outer surface of the capillary component using a deposition process (e.g., a chemical vapor deposition (CVD) process, a sputtering process). In some embodiments, the coating can be disposed on the outer surface of the capillary component by dipping the capillary component into a material that defines the coating. In some embodiments, a coating can be disposed outside of a distal end portion of a side-fire member shown in, for example, FIG. 2.

Figure 7:
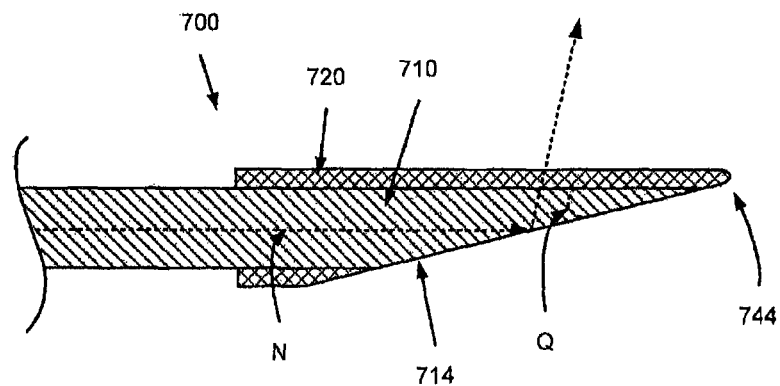
FIG. 7 is a schematic diagram that illustrates a side cross-sectional view of a distal end portion of a side-fire member with a capillary component defining at least a portion of an angled surface, according to an embodiment.

FIG. 7 is a schematic diagram that illustrates a side cross-sectional view of a distal end portion 700 of side-fire member with a capillary component 720 defining at least a portion of an angled surface 714, according to an embodiment. As shown in FIG. 7, at least a portion the capillary component 720 and at least a portion of an optical waveguide 710 define the angled surface 714. The angled surface 714 is defined so that at least a portion of laser energy N propagated within the optical waveguide 710 is redirected by an interface defined by the angled surface 714 and a fluid distal to the angled surface 714. In some embodiments, when used during a medical procedure the fluid can be a fluid inside of a body of a patient and in contact with the angled surface 714.

The distal end portion 700 of the side-fire member shown in FIG. 7 is different (at least in part) than the distal end portions of side-fire members shown in, for example, FIGS. 2 and 5 in that the capillary component 720 does extend beyond (e.g., distal to) a plane aligned with the angled surface 714 and does not define an enclosure. Instead, the capillary component 720 defines a portion of the angled surface 714 and the capillary component 720 is coterminous with the angled surface 714 of the optical waveguide 710. Because the capillary component 720 does not extend beyond the angled surface 714, damage that could otherwise be inflicted on a portion of a capillary component that extends beyond the angled surface 714 (and is not otherwise reinforced as described herein) can be avoided.

In some embodiments, an angle Q can be between 5 and 20 degrees (e.g., approximately 15 degrees). The angle Q can be referred to as an angle of the angled surface 714. In some embodiments, the angle Q can be defined so that laser energy propagated within the optical waveguide 710 (such as laser energy N) will be redirected in substantially a lateral direction relative to a longitudinal axis or centerline of the optical waveguide 710. At least a portion of laser energy N will be redirected at an interface defined by the angled surface 714 and water distal to the angled surface 714 when the angle Q is approximately 13 degrees.

In some embodiments, the capillary component 720 can be cut from a preform similar to (or the same as) that described in connection with FIG. 3A. The capillary component 720 can be moved over the distal end of the optical waveguide 710. The angled surface 714 can be defined after an inner surface of the capillary component 720 is heat fused to an outer surface of the optical waveguide 710.

As shown in FIG. 7, a tip 744 of the distal end portion 700 of the side-fire member is polished so that it defines a blunt edge (e.g., atraumatic edge). In this embodiment, the tip 744 is polished so that it defines a radius. In other words, a sharp edge that is typically defined when the angled surface 714 is formed can be polished so that the sharp edge is removed. The tip 744 may be polished so that the tip 744 may not, for example, puncture a body of a patient or a sheath of an endoscope during use. In some embodiments, other portions of an edge of the angled surface 714 (such as any circumferential portion of an edge of the capillary component 720) can be polished so that they have a desirable radius and/or are not sharp. In some embodiments, the edges of the capillary component 720 can be outside of path of some or all of laser energy N that may be redirected through the capillary component. Accordingly, the edge of the capillary component 720 can be considered sacrificial in the sense they can be chipped, scratched, and/or polished during use and/or manufacturing without undesirable deterioration of the optical properties of the distal end portion 700 of the side-fire member.

Although not shown in FIG. 7, in some embodiments, an optical waveguide can be cleaved (and/or polished) so that it defines an angled surface before the capillary component is moved over the angled surface of the optical waveguide. In such embodiments, the capillary component (which can have straight edges that are substantially normal to a longitudinal axis (or centerline) of the capillary component) can be heat-fused to the optical waveguide after the capillary component is disposed over the angled surface. After the capillary component is heat-fused to the optical waveguide, a distal end of the capillary component may be disposed within a plane that is non-parallel to the angled surface of the optical waveguide. For example, the capillary component can have a distal end surface that is substantially normal to a longitudinal axis (or centerline) of the optical waveguide. In such embodiments, a relatively small portion of the capillary component can extend beyond the angled surface of the optical waveguide. In such embodiments, a distal end surface of the capillary component may be non-parallel to the angled surface of the optical waveguide and a portion of the distal end surface can be coterminous with a portion of the angled surface.

Figure 8:
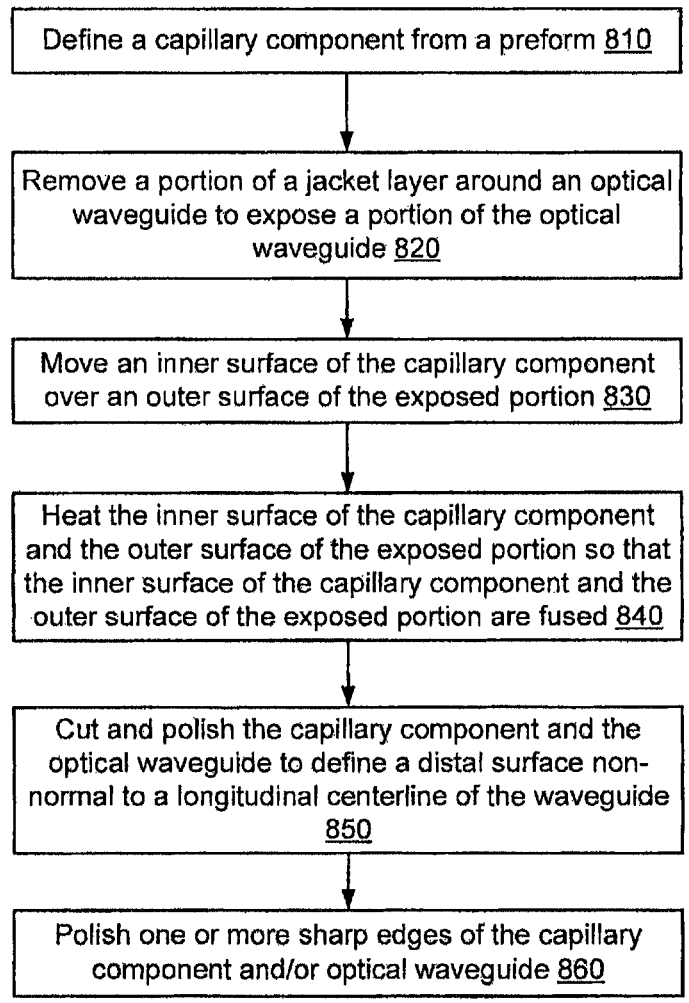
FIG. 8 is a schematic diagram that illustrates a method for producing a side-fire member with a capillary component defining at least a portion of an angled surface, according to an embodiment.

FIG. 8 is a schematic diagram that illustrates a method for producing a side-fire member with a capillary component defining at least a portion of an angled surface, according to an embodiment. As shown in FIG. 8, a capillary component can be defined from a preform, at 810. The capillary component can be cut from a preform that can be doped with, for example, fluorine or another dopant.

A portion of a jacket layer around an optical waveguide can be removed to expose a portion of the optical waveguide, at 820. In some embodiments, the jacket layer can be removed to expose a buffer layer and/or a cladding layer of the optical waveguide.

An inner surface of the capillary component can be moved over an outer surface of the exposed portion, at 830. The capillary component can be moved so that a few millimeters or centimeters of the exposed portion of the optical waveguide is covered.

The inner surface of the capillary component and the outer surface of the exposed portion can be heated so that the inner surface of the capillary component and the outer surface of the exposed portion are fused, at 840. In some embodiments, an entire outer surface of the optical waveguide that is disposed within the capillary component can be heat-fused to the inner surface of the capillary component. In some embodiments, less than an entire outer surface of the optical waveguide that is disposed within the capillary component can be heat-fused to the inner surface of the capillary component. In other words, only a portion of the outer surface of the optical waveguide that is disposed within the capillary component can be heat-fused to the inner surface of the capillary component.

The capillary component and the optical waveguide can be cut and polished to define a distal surface non-normal to a longitudinal centerline of the waveguide, at 850. In other words, the capillary component and the optical waveguide can be cut and polished so that they collectively define an angled surface. In some embodiments, the angled surface can have an angle of approximately 13 degrees.

One or more sharp edges of the capillary component and/or optical waveguide can be polished, at 860. In some embodiments, for example, a tip of the side-fire member can be polished so that the tip defines a blunt edge (e.g., a flat portion, a radius).

Although not shown in FIG. 8, in some embodiments, the optical waveguide can be cleaved (and/or polished) so that it defines an angled surface before the capillary component is moved over the angled surface of the optical waveguide. In such embodiments, the capillary component may be heat-fused to the optical waveguide after the capillary component is disposed over the angled surface. After the capillary component is heat-fused to the optical waveguide, a distal end of the capillary component may be disposed within a plane that is non-parallel to the angled surface of the optical waveguide. In some embodiments, the capillary component can be covered with a coating such as that described in connection with FIGS. 5 and 6.

Figure 9:
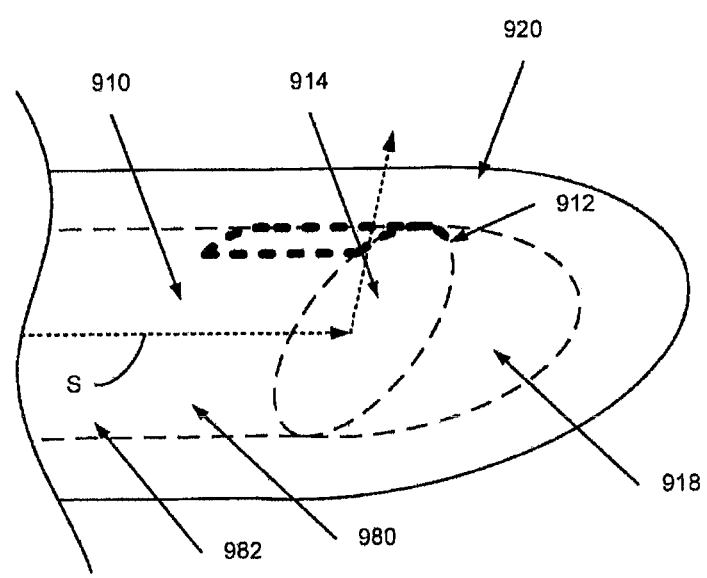
FIG. 9 is a schematic diagram that illustrates a portion of an optical waveguide that is heat-fused to a capillary component, according to an embodiment.

FIG. 9 is a schematic diagram that illustrates a portion of an optical waveguide 910 that is heat-fused to a capillary component 920, according to an embodiment. As shown in FIG. 9, the optical waveguide 910 defines an angled surface 914 and the angled surface 914 defines at least a portion of an enclosure 918. The heat-fused region 912 is a region through which at least a portion of laser energy S can be redirected at an interface defined by the angled surface. 914 and a fluid in the enclosure 918. As shown in FIG. 9, the heat-fused region does not extend around the entire circumference of a cross-sectional portion of the optical waveguide 910.

As shown in FIG. 9, other portions of the optical waveguide 910 such as region 980 (unlike heat-fused region 912) are not heat-fused to the capillary component 920. The other portions of the optical waveguide 910 are not heat-fused to the capillary component 920 so that un-fused portions of the capillary component 920 may be more free to flex than if the other portions of the optical waveguide 910 (such as region 980) were heat-fused to the capillary component 920. In other words, a relatively stiff to relatively flexible section transition that exists when the entire circumference of a cross-sectional portion of the optical waveguide 910 is heat-fused to the inner surface of the capillary component 720 is reduced (e.g., minimized). Portions of the capillary component 920 are more free to expand and/or contract than if the entire circumference of a cross-sectional portion the optical waveguide 910 were heat-fused to the capillary component 920.

As shown in FIG. 9, at least some portions of the optical waveguide 910 that are not heat-fused to the capillary component 920 are in contact with the capillary component 920. For example, region 980 of the optical waveguide 910 is in contact with an inner surface of the capillary component 920. Also, as shown in FIG. 9, a region of the optical waveguide 982, which is on a side of the optical waveguide 910 is that is opposite that of the heat-fused region 912, is in contact with an inner surface of the capillary component 920.

In some embodiments, a reinforcement component such as that shown in FIG. 2 can be coupled to an inner surface of the capillary component 920 shown in FIG. 9. In such embodiments, the reinforcement component can be heat-fused to the capillary component 920 in a fashion that mirrors that of the heat-fusing of the optical waveguide 910 to the capillary component 920. For example, if only a top portion of the optical waveguide 910 is heat-fused to the capillary component 920 as shown in FIG. 9, a reinforcement component distal to the optical waveguide 910 can similarly have only a top portion heat-fused to the capillary component 920. A surface area of a region of the optical waveguide 910 heat-fused to the capillary component 920 can be the same (e.g., substantially the same) or different than a surface area of a region of the reinforcement component heat-fused to the capillary component 920.

While various embodiments have been described above, it should be understood that they have been presented by way of example only, not limitation, and various changes in form and details may be made. Any portion of the apparatus and/or methods described herein may be combined in any combination, except mutually exclusive combinations. The embodiments described herein can include various combinations and/or sub-combinations of the functions, components and/or features of the different embodiments described. For example, heat-fusing of a capillary component to a reinforcement component and/or optical waveguide can be performed simultaneously using multiple heat sources.

Other embodiments will be apparent to those skilled in the art from consideration of the specification and practice of the embodiments disclosed herein. It is intended that the specification and examples be considered as exemplary only, with a true scope and spirit of the invention being indicated by the following claims.

What is claimed is:

1. An apparatus comprising:
   an optical waveguide including a distal end portion extending continuously along a longitudinal axis, the distal end portion having a distal end surface non-normal to the longitudinal axis, the distal end surface defining a proximal portion of an interface configured to redirect electromagnetic radiation out of the optical waveguide in a direction lateral to the longitudinal axis;
   a reinforcement component having a proximal end surface disposed distal to the distal end surface of the optical waveguide, the proximal end surface defining a distal portion of the interface;
   a gap disposed between the distal end surface of the optical waveguide and the proximal end surface of the reinforcement component, the gap having a non-zero width along the longitudinal axis; and
   a capillary component with (i) a first interior surface coupled to an outer surface of the optical waveguide along a first length extending proximally from the distal end surface of the optical waveguide, and (ii) second interior surface coupled to an outer surface of the reinforcement component along a second length extending distally from the proximal end surface of the reinforcing component,
   wherein the gap is sealed by the capillary component, and the interface includes a fluid sealed in the gap.

2. The apparatus of claim 1, wherein the reinforcement component includes an outer diameter substantially the same as an outer diameter of the optical waveguide.

3. The apparatus of claim 1, wherein the gap is sealed by an interior surface of the capillary component disposed between the first and second lengths, a third portion of the inner surface of the capillary component and a distal end surface of the reinforcement component define an enclosure, and the gap is fluidically isolated from the enclosure.

4. The apparatus of claim 1, wherein the distal end surface of the optical waveguide is substantially parallel to the proximal end surface of the reinforcement component.

5. The apparatus of claim 1, wherein the proximal end surface of the reinforcement component comprises a reflective material.

6. The apparatus of claim 1, wherein the first interior surface of the capillary component is heat-fused to the outer surface of the optical waveguide along the first length, and the second interior surface of the capillary component is heat-fused to the outer surface of the reinforcement component along the second length.

7. The apparatus of claim 1, wherein an entire circumference of a cross-sectional portion of the optical waveguide is heat-fused to the first portion of the inner surface of the capillary component along the first length.

8. The apparatus of claim 7, wherein an entire circumference of a cross-sectional portion of the reinforcement component is heat-fused to the second portion of the inner surface of the capillary component along the second length.

9. An apparatus, comprising:
   an optical waveguide including a distal end portion extending continuously along a longitudinal axis, the distal end portion including a distal end surface non-normal to the longitudinal axis, the distal end surface defining a first portion of an interface configured to redirect electromagnetic radiation propagated from within the optical waveguide and incident on the portion of the interface to a direction offset from the longitudinal axis;
   a reinforcement component having a proximal end portion including a proximal end surface disposed distal to the distal end surface of the optical waveguide, the proximal end surface defining a second portion of the interface;
   a capillary component coupled to (i) the distal end portion of the optical waveguide along a first length extending proximally from said distal end surface, and (ii) the proximal end portion of the reinforcing component along a second length extending distally from said proximal end surface;
   a gap sealed between the distal end surface of the optical waveguide, the proximal end surface of the reinforcing component, and an interior surface of capillary component; and
   a fluid sealed in the cap.

10. The apparatus of claim 9, wherein the reinforcement component includes a hardness substantially corresponding to a hardness of a core portion of the optical waveguide.

11. The apparatus of claim 9, wherein an entire circumference of a cross-sectional portion of the optical waveguide is heat-fused to the first portion of the inner surface of the capillary component.

12. An apparatus, comprising:
   an optical waveguide including a distal end portion extending continuously along a longitudinal axis, the distal end portion including a distal end surface that defines a proximal portion of an energy redirecting interface configured to redirect laser energy out of the waveguide in a direction lateral to the longitudinal axis;
   a reinforcement component including a proximal end portion with a proximal end surface that defines a distal portion of the energy redirecting interface;
   a capillary component with (i) a proximal interior surface coupled to an exterior surface of the distal end portion of the optical waveguide along a first length extending proximally from the proximal portion of the energy redirecting interface, and (ii) a distal interior surface coupled to an outer surface of the proximal end portion of the reinforcement component along a second length extending distally from the distal portion of the energy redirecting interface; and a gap located between the distal end surface of the optical waveguide and the proximal end surface of the reinforcing component, wherein gap is sealed by the capillary component, and the energy redirecting interface includes a fluid sealed in the gap.

13. The apparatus of claim 12, further comprising an enclosure sealed between a distal end surface of the reinforcing member and the distal interior surface of the capillary component, wherein the gap is fluidically isolated from the enclosure.

* * * * *